(12) United States Patent
Masahiro

(10) Patent No.: US 11,083,431 B2
(45) Date of Patent: Aug. 10, 2021

(54) RADIATION FLUOROSCOPY IMAGING APPARATUS

(71) Applicant: SHIMADZU CORPORATION, Kyoto (JP)

(72) Inventor: Tanaka Masahiro, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 104 days.

(21) Appl. No.: 15/903,689

(22) Filed: Feb. 23, 2018

(65) Prior Publication Data

US 2019/0261941 A1 Aug. 29, 2019

(51) Int. Cl.
*A61B 6/00* (2006.01)
*A61B 6/06* (2006.01)

(52) U.S. Cl.
CPC ............... *A61B 6/548* (2013.01); *A61B 6/06* (2013.01); *A61B 6/405* (2013.01); *A61B 6/461* (2013.01); *A61B 6/485* (2013.01); *A61B 6/487* (2013.01)

(58) Field of Classification Search
None
See application file for complete search history.

(56) References Cited

U.S. PATENT DOCUMENTS

| | | | |
|---|---|---|---|
| 6,934,363 B2 * | 8/2005 | Seufert | G21K 1/04 378/147 |
| 2014/0341348 A1 * | 11/2014 | Kawano | A61B 6/06 378/62 |
| 2015/0078524 A1 * | 3/2015 | Shimizu | A61B 6/467 378/62 |
| 2017/0181720 A1 * | 6/2017 | Akiyama | A61B 6/467 |

FOREIGN PATENT DOCUMENTS

| | | |
|---|---|---|
| JP | 05-161629 | 6/1993 |
| JP | 7-8482 | 1/1995 |
| JP | H7-8482 | 1/1995 |
| JP | 2013-128585 | 7/2013 |

OTHER PUBLICATIONS

JP 2015-177468, Notice of Reasons for Refusal dated Nov. 28, 2018, 3 pages—Japanese, 3 pages—English.

* cited by examiner

*Primary Examiner* — Hoon K Song
(74) *Attorney, Agent, or Firm* — Andrew F. Young, Esq.; Nolte Lackenbach Siegel

(57) ABSTRACT

An X-ray fluoroscopy imaging apparatus that confirms the radiation field of a radiation imaging when an operator performs an examination in an operation room. A collimator 12 has a plurality of collimator-leaves 61 positioned and forming a first X-ray radiation field E1 while performing an X-ray fluoroscopy. The apparatus allows an operator, in an operating room distant from an imaging room, to operate an aperture change to confirm the radiation field and each of the collimator-leaves 61 shifts to a position where the X-ray radiation field is reduced to a smaller dimension field E2. Visualizing a displayed X-ray image allows the operator to confirm reaching the radiation field E2.

2 Claims, 8 Drawing Sheets

RADIATION FLUOROSCOPY IMAGING APPARATUS

CROSS REFERENCE TO RELATED APPLICATIONS

This application relates to, but does not claim priority from, JP 2015-177468 filed Sep. 9, 2015 and published on Mar. 16, 2017, the entire contents of which are incorporated herein by reference.

FIGURE SELECTED FOR PUBLICATION

FIGS. 7A, 7B

BACKGROUND OF THE INVENTION

Field of the Invention

The present invention relates to a radiation fluoroscopy imaging apparatus that performs a radiation fluoroscopy and a radiation imaging for a subject.

Description of the Related Art

For example, the X-ray fluoroscopy imaging apparatus that performs an X-ray fluoroscopy and an X-ray imaging for the subject comprises an X-ray tube that irradiates an X-ray toward the subject, an X-ray detector, such as a flat panel detector and an image intensifier (I. I.) and so forth, that detects the X-ray that transmits the subject, a plurality of collimator-leaves, which changes the area (range) size of the X-ray that is irradiated toward the subject, in-place between the X-ray tube and the subject. Such X-ray imaging element is located in the examination room. In addition, such X-ray fluoroscopy imaging apparatus comprises a display element that displays the image acquired by the X-ray detector and a controller that controls a variety of operations for the X-ray imaging, including the operation for an aperture of the collimator-leaves. Such display element and the controller are located in the examination room.

Relative to such X-ray fluoroscopy imaging apparatus, the X-ray radiation field (exposure field) during X-ray fluoroscopy and the X-ray radiation field on the X-ray imaging are generally different from each other. Therefore, when switching to the X-ray imaging while performing the X-ray fluoroscopy, the operator cannot make sure which range is to be imaged. Accordingly, in case, the operator must adjust the imaging range by the X-ray fluoroscopy again following switching to the X-ray imaging.

On the other hand, relative to such X-ray fluoroscopy imaging apparatus, a collimator lamp is used to make sure the range of the X-ray radiation field. Such collimator lamp is in-place at the conjugate location of the focal point of the X-ray tube via such as a half-mirror and so forth, and the light exposure field of the light that is irradiated from the collimator lamp and of which the irradiation range is limited by the collimator-leaves is confirmed, so that the X-ray radiation field can be checked.

In addition, the Patent Document 1 discloses the X-ray fluoroscopy imaging platform, wherein once the collimator lamp switch is pressed down; the collimator light is turned on and the collimator-leaves shift to the location corresponding to the imaging size based on the film, and subsequently, the collimator light is turned off, the collimator shifts to the location corresponding to the imaging size based on the I. I.

RELATED PRIOR ART DOCUMENTS

Patent Document
Patent Document 1: JP Patent Published H7-8482 A

ASPECTS AND SUMMARY OF THE INVENTION

Objects to be Solved

With regard to the X-ray fluoroscopy imaging platform according to the Patent Document 1 as described above, when the operator is in the examination room and the method, by which the X-ray radiation field during the X-ray fluoroscopy and on the X-ray imaging is checked, is applied, and the operator can check the X-ray radiation, but when the operator is in the operation (different) room, the operator cannot accurately check the X-ray radiation field. Therefore, when the operator performs the examination in the operation room and switches the X-ray fluoroscopy to the X-ray imaging while performing the X-ray fluoroscopy, the operator is too hard to make sure which range is to be imaged. Accordingly, in case, the operator must adjust the imaging range by the X-ray fluoroscopy again following switching to the X-ray imaging.

The purpose of the present invention is to solve the above objects and to provide an X-ray fluoroscopy imaging apparatus that facilitates the operator to make sure the radiation field of the radiation on the X-ray imaging while performing the X-ray fluoroscopy even when the operator carries out the examination in the operation room.

Means for Solving the Problem

According to the invention claimed herein, an X-ray fluoroscopy imaging apparatus that is located in an examination room, comprises; a radiation source that irradiates a radiation to a subject, a radiation detector that detects a radiation that is irradiated from the radiation irradiation element and transmits through the subject, a plurality of collimator-leaves in-place between the radiation irradiation element and the subject, and a collimator that changes the area size of the radiation that is irradiated from the radiation irradiation element to the subject; and an X-ray imaging apparatus that is located in an operation room further comprises a display element that displays an image that the radiation detector acquires, an aperture change switch that is located in the operation room and changes an aperture of the collimator-leaves, and further comprises a control element that changes the aperture of the collimator-leaves to the aperture for performing an radiation imaging when the aperture change switch is operative while performing the X-ray fluoroscopy.

According to another aspect of the present invention, a radiation fluoroscopy imaging apparatus is provided wherein; the control element changes back the aperture of the collimator-leaves to the aperture that is the aperture while performing the radiation fluoroscopy following passing of constant time or re-operation of the aperture changing switch since then the aperture of the collimator-leaves is changed to the aperture for the radiation imaging by the operation of the aperture changing switch.

Effect of the Invention

According to another aspect of the present invention, a radiation fluoroscopy imaging apparatus is provided, and when the operator performs the radiation fluoroscopy and the radiation imaging even in the operation room, the operator can facilitate confirmation of the radiation field of the radiation on the radiation imaging while performing the radiation fluoroscopy based on the image displayed on the display element.

According to the aspect of the present invention, the operator can continuously perform the radiation fluoroscopy following confirmation of the radiation field of the radiation on the radiation imaging.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1A:
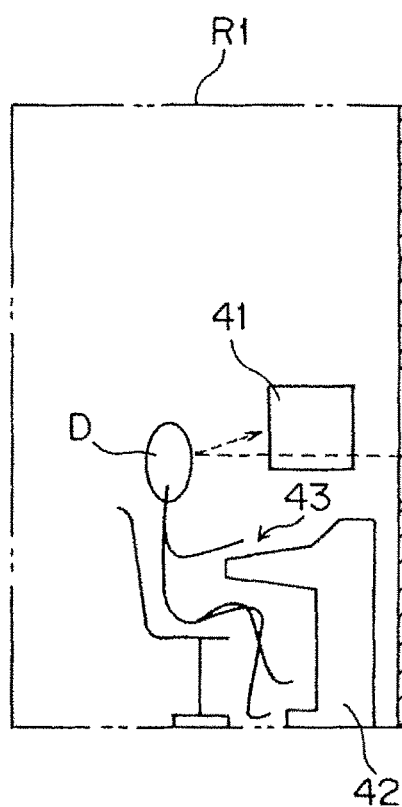
FIG. 1A, FIG. 1B are schematic views illustrating an X-ray fluoroscopy imaging apparatus as a radiation fluoroscopy imaging apparatus according to the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, a "computer-involved apparatus" includes, without limitation an input device for receiving data of any kind, an output device for outputting data in any tangible form (e.g. data stream, image representations, database updates, or as knotted herein below or by printing or displaying on a computer screen), a memory for storing data as well as computer code, and a processor for executing computer code wherein any computer code resident in a memory will physically cause the processor to change and to read-in data via an input device (e.g., including via a fluoroscopy imaging imager-device), process data within the processor and output processed data via an output output device such as a viewing image screen which is changed to show the output image generated.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents (resistors, capacitors, transistors, heat sinks, etc.) noted herein and structures that accomplish the functions without restrictive language or label requirements since those of skill in the art are well versed in related radiation fluoroscopy imaging apparatus and devices, computer and operational controls and technologies of radiographic devices and all their sub components, including various circuits and combinations of circuits without departing from the scope and spirit of the present invention.

Although only a few embodiments have been disclosed in detail, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, elements, or circuits described in connection with the embodiments disclosed herein (e.g., logic blocks are circuits or elements following and actuating that logic), may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

Figure 1B:
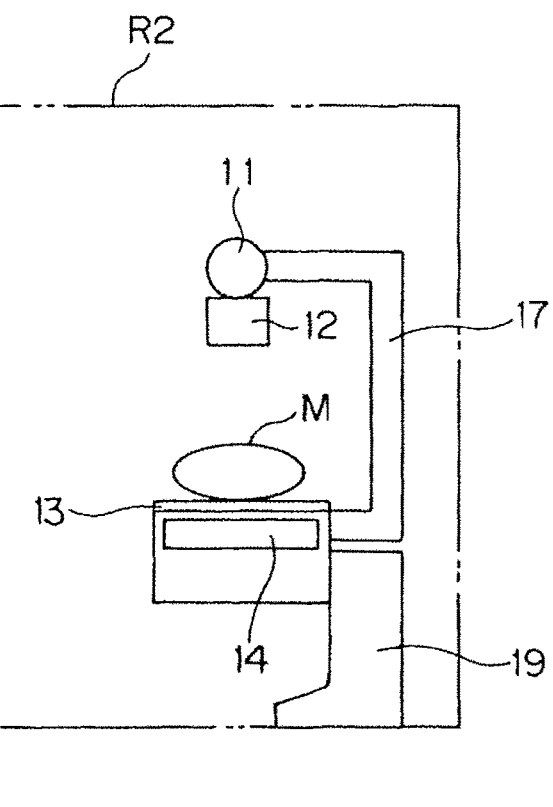

The inventor sets forth Embodiments of the present invention based on the following FIGs. FIG. 1A, FIG. 1B are schematic views illustrating an X-ray fluoroscopy imaging apparatus as a radiation fluoroscopy imaging apparatus according to the present invention. In addition, FIG. 2 is a perspective view of the fluoroscopy imaging platform in-place in the examination room R2.

Such an X-ray imaging apparatus that performs the X-ray imaging and the X-ray fluoroscopy for the subject M comprises one or more controllers having the operation panel 43 and the display element 41 in the operation room R1 and the fluoroscopy platform that is located in the examination room R2. The imaging room R1 and the operation room R2 are separated by the partition-wall 21 from each other. Such partition-wall 21 has a window 22 made of the lead-glass capable of blocking the X-ray, and the operator can make sure the inside state of the examination room R2 through the lead-glass window.

The controller 42 that is located in the operation room R1, as set forth later, comprises a control element 40 that controls the entire apparatus. The operation panel 43 that is used to execute a variety of operations, set forth later, is attached to the controller 42. In addition, the display element 41 that is located in the operation room R1 comprises a liquid crystal display panel and displays the X-ray image that the X-ray detector 14 acquires.

Figure 2:
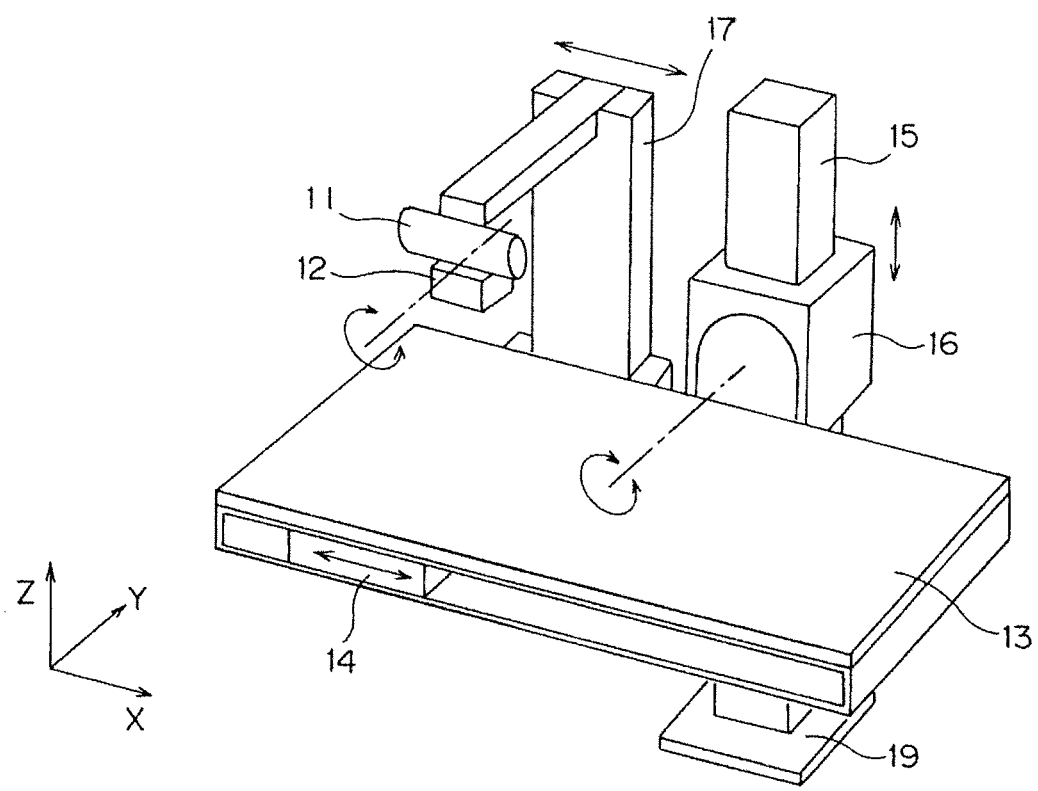
FIG. 2 is a perspective view of the fluoroscopy imaging platform installed in the examination room R2.

Referring to FIG. 2, the X-ray fluoroscopy imaging platform that is located in the examination room R2 comprises a main support column 15 that is installed upright on the base 19, a holding member 16 that is liftable and lowerable relative to the main support column 15, a table 13 that is rotatably connected to the holding member 16, a support column 17 that supports the X-ray tube 11 and the collimator 12, and an X-ray detector 14 such as a flat panel detector and so forth that is in-place below the surface of the table 13 and facing the X-ray tube 11. Further, referring to FIG. 1, the main support column 15 and the holding member 16 are not shown.

In addition, the holding member 16 lifts and lowers in the Z-direction referring to FIG. 2. In addition, the table 13 rotates around the axis which is orthogonal to the longitudinal direction of the table 13 and facing the horizontal direction (axis in the direction facing Y-direction in FIG. 2). In addition, the support column 17 and the X-ray detector 14 shifts back-and-forth in synchronism with each other in the longitudinal direction of the table 13. In addition, the X-ray tube 11 and the collimator 12 lift and lower along with the support column in the Z-direction (referring to FIG. 2). In addition, the X-ray tube 11 and the collimator 12 are oscillatable above the table 13 and are supported by the support column 17.

Figure 3:
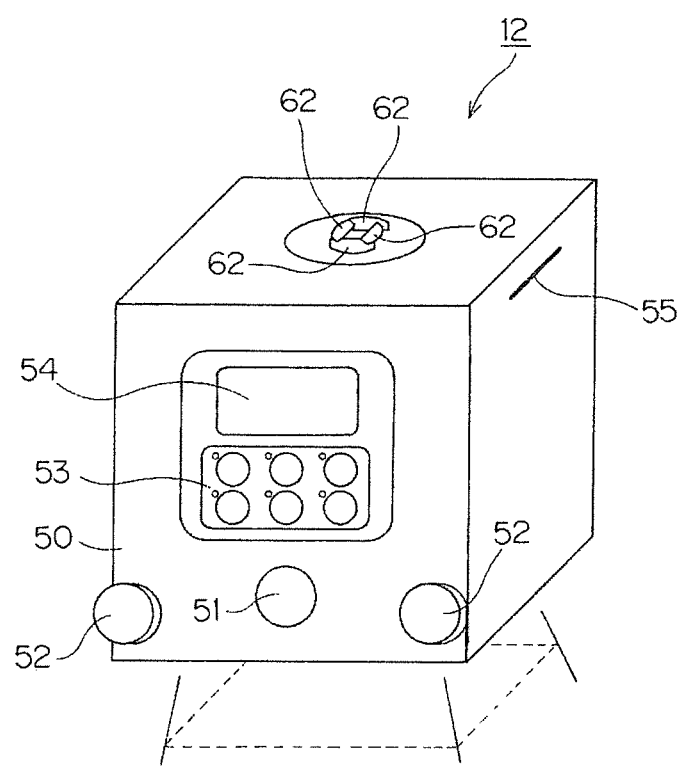
FIG. 3 is a perspective view illustrating the collimator 12.
Figure 4:
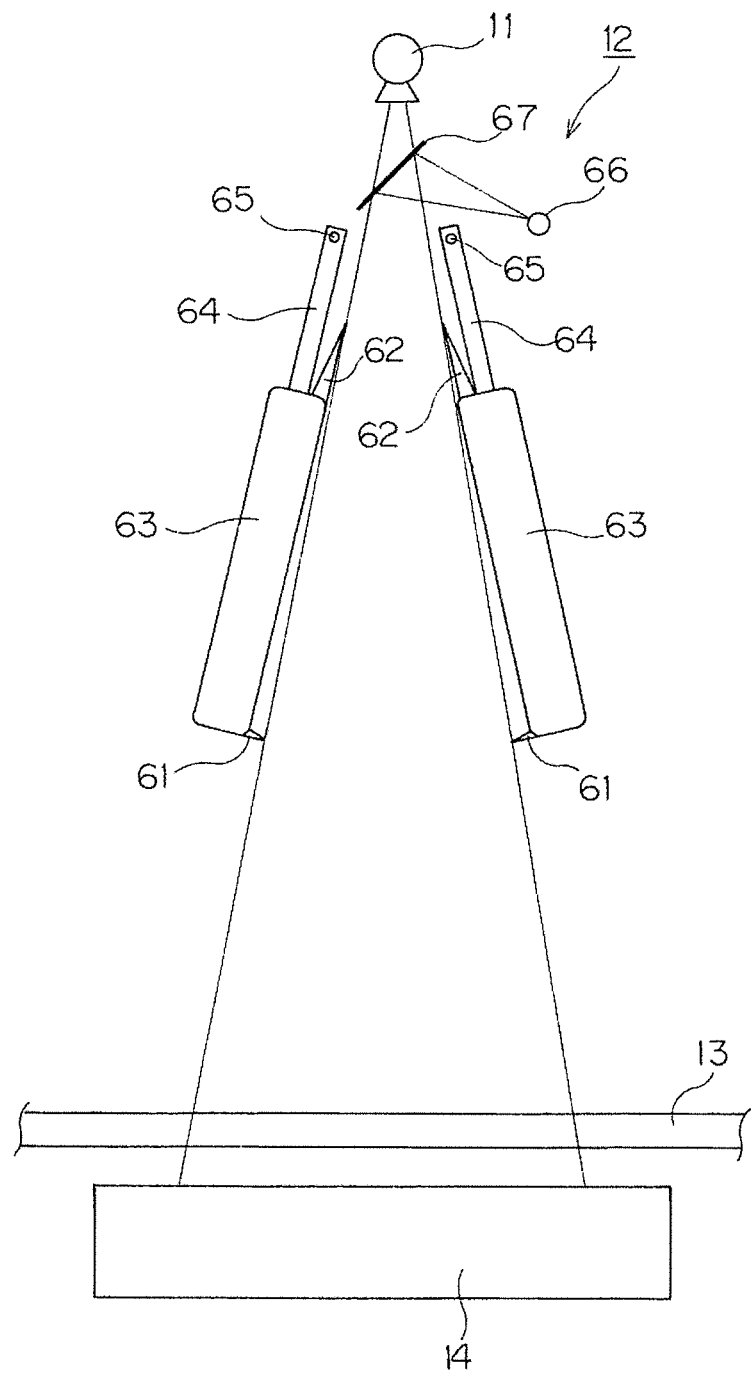
FIG. 4 is a schematic view illustrating the inside structure of the collimator 12 and the X-ray tube 11.

FIG. 3 is a perspective view illustrating the collimator 12. FIG. 4 is a schematic view illustrating the inside structure of the collimator 12 and the X-ray tube 11.

Referring to FIG. 3, such collimator 12 comprises a radiation field lamp button 51 to turn on the collimator lamp 66 shown in FIG. 4, a pair of diaphragm adjusters 52 that adjust the X-ray radiation field by oscillating a plurality of shifting members 63 facing each other among the shifting members 63 (shown in FIG. 4), multipurpose switches 53 that are operative to carry out a variety of operations including an operation to change an aperture dimension of the collimator-leaves 61 (as set forth later), and an operation panel 50 including the liquid crystal display element 54. In addition, the collimator 12 further comprises an additional filter insertion opening 55 to insert an additional filter.

Referring now additionally to FIG. 4, the collimator 12 comprises four shifting members 63, with pairs of shifting members 63 facing each other in an opposed manner to define sides of an aperture. Only two shifting members 63, 63 are shown facing each other are shown in FIG. 4. Each shifting member 63 is connected to a movement axis 65 through a connection member 64 and is oscillatable relative to the movement axis 65 as a movement center therefor. A diaphragm 62 is attached to the top of each shifting member 63. A collimator-leaf 61 is attached to a bottom of each of the shifting member 63. Each opposed pair of shifting members 63, 63 faces each other and is orthogonal to the other opposed pair of shifting members 63, 63 so that a rectangular aperture region is formed with the collimator-leaves 61.

The collimator-leaves 61 limit further the radiation field following limitation of the radiation field of the X-ray irradiated from the X-ray tube 11 using the diaphragms 62 and consequently, form a rectangular X-ray radiation field when the subject M is irradiated. In such a way, both the diaphragms 62 and the collimator-leaves 61 block the X-ray and form the X-ray radiation field together, with security, so that a leakage of the X-ray can be absolutely prevented, and the X-ray radiation field can be correctly formed.

In addition, a mirror 67 is in-place in the X-ray radiation field and the collimator lamp 66 is in-place at the location facing the mirror 67. When the collimator lamp 66 is turned on, the light from the collimator lamp 66 is irradiated toward the collimator-leaves 61 via the mirror 67, so that the light radiation field corresponding to the X-ray radiation field is formed. Accordingly, the operator can make sure utilizing the light radiation field in the examination room R2 whether the X-ray radiation field is adequately formed or not.

Figure 5:
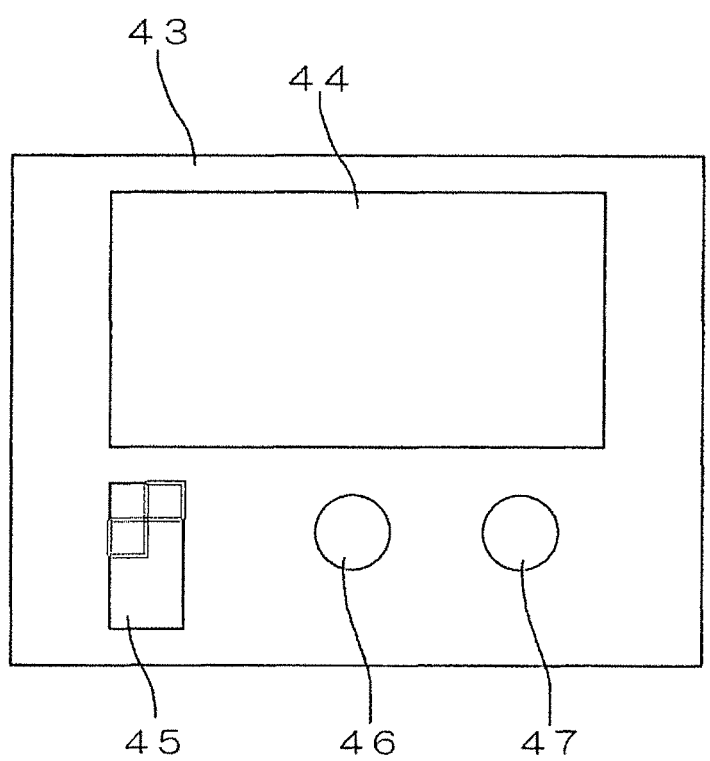
FIG. 5 is a schematic view illustrating the operation panel 43 relative to a controller 42 in-place in the operation room R1.

FIG. 5 is a schematic view illustrating the operation panel 43 relative to a controller 42 in-place in the operation room R1.

The operation panel 43 comprises the liquid crystal display element 44, the diaphragm adjuster 45 that adjusts the X-ray radiation field by oscillating the opposed shifting members 63 facing each other among the four shifting members 63 (two shown in FIG. 4), a radiation field lamp button 46 that turns on the collimator lamp 66 shown in FIG. 4, and the aperture change switch 47 that changes the aperture of the collimator-leaves 61 to the aperture on the X-ray imaging while performing the X-ray fluoroscopy.

Figure 6:
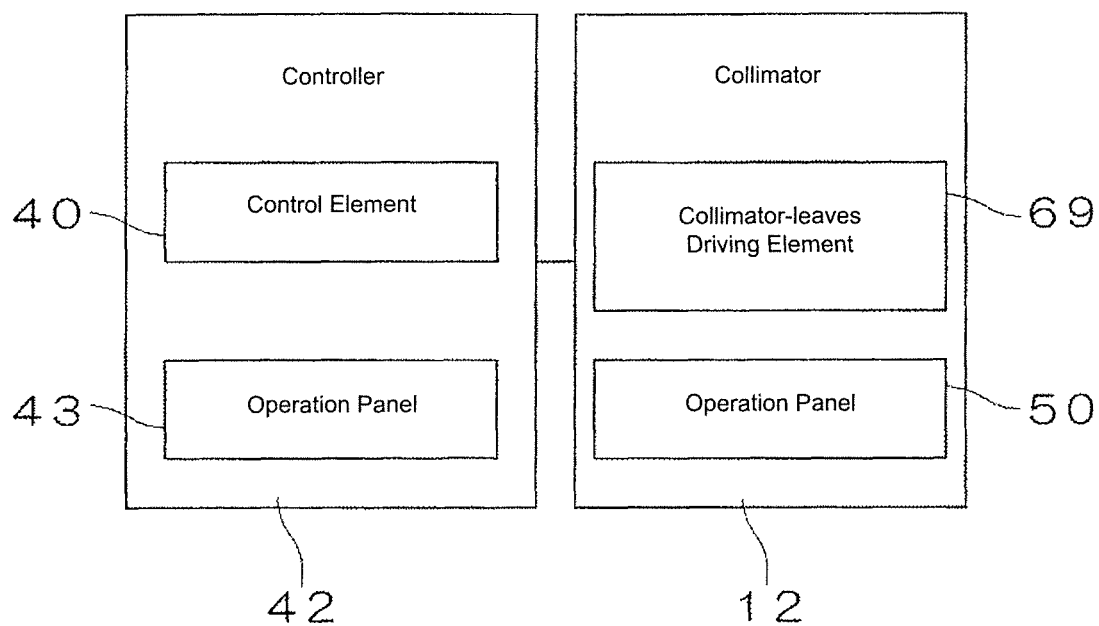
FIG. 6 is a block diagram illustrating the main control system of the X-ray fluoroscopy imaging apparatus according to the aspect of the present invention.

FIG. 6 is a block diagram illustrating the main control system of the X-ray fluoroscopy imaging apparatus according to the aspect of the present invention.

The controller 42 that is located in the operation room R1 comprises a control element 40 that controls the entire apparatus. In addition, the collimator 12 that is located in the examination room R2 further comprises a collimator-leaves driving element 69 that is installed and operates each of the above shifting members 63 and respectively open-and-closes each of the collimator-leaves 61 by oscillation. Both the operation panel 43 of the controller 42 and the operation panel 50 of the collimator 12 are operable to execute the open-and-close operation of the collimator-leaves 61 and the lighting operation of the collimator lamp 66.

When the X-ray fluoroscopy is performed using the X-ray fluoroscopy imaging apparatus having such above aspects, the operator D operates the operation panel 43 of the controller 42 located in the operation room R1 to adjust the aperture and position of the collimator-leaves 61. Then, the display element 41 displays the X-ray fluoroscopic image that the X-ray detector 14 detects.

The case in which the X-ray imaging is performed while performing such X-ray fluoroscopy may take place. At that initial time, when switching the X-ray fluoroscopy to the X-ray imaging while performing the X-ray fluoroscopy, the radiation field of the X-ray fluoroscopy and the radiation field of the X-ray imaging are generally different from each other, so that the operator D, who is in the examination room R1, cannot make sure which range is subjected to imaging. Therefore, the X-ray fluoroscopy imaging apparatus, according to the aspect of the present invention, changes the initial aperture of the collimator-leaves 61 to the controlled aperture for performing a radiation imaging by controlling the control element 40 when the aperture change switch 47 of the operation panel 43 is operative while performing the X-ray fluoroscopy.

Figure 7A:
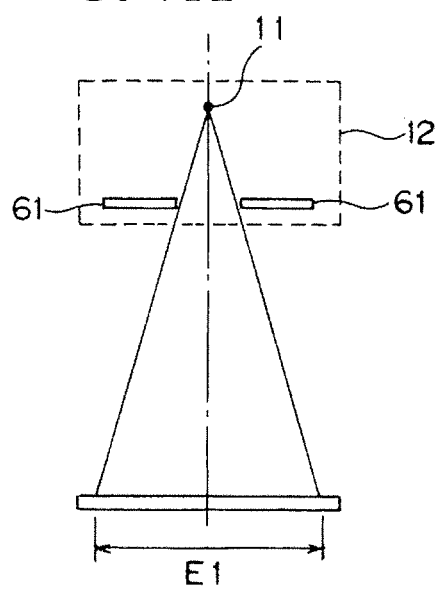
FIG. 7A, FIG. 7B are schematic views illustrating the changing state of the X-ray radiation field changed by the collimator 12.
Figure 7B:
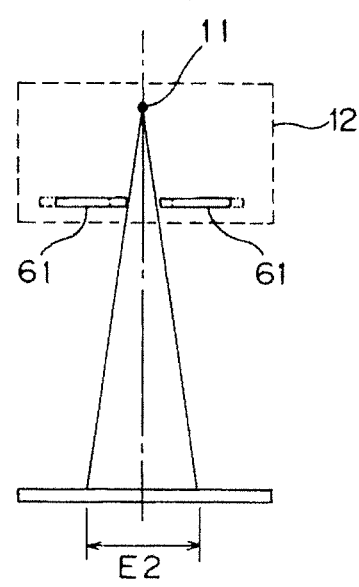
Figure 8A:
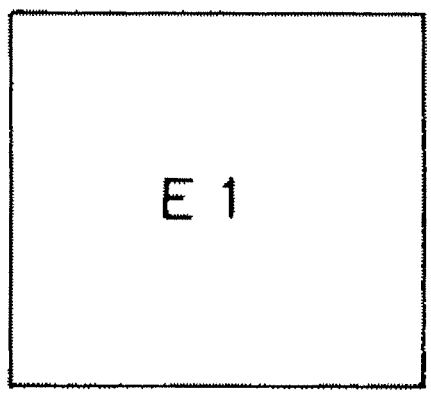
FIG. 8A, FIG. 8B are schematic views illustrating the X-ray radiation field E1 on the X-ray fluoroscopy and the X-ray radiation field E2 on the X-ray imaging.
Figure 8A:
Figure 8B:
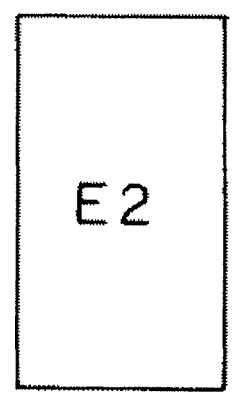

FIG. 7A, FIG. 7B are schematic views illustrating the changing state of the X-ray radiation field changed by the collimator 12, and FIG. 8A, FIG. 8B are schematic views illustrating the X-ray radiation field E1 on the X-ray fluoroscopy and the X-ray radiation field E2 on X-ray imaging.

Referring to FIG. 7A, the collimator-leaves 61 of the collimator 12 are in-place in the position at which the X-ray radiation field E1 on the X-ray fluoroscopy is formed while performing the X-ray fluoroscopy. Under such state, when the operator D, who is operating in the operation room R1, operates the aperture change switch 47 to make sure the radiation field on the X-ray imaging, the control element 40 controls that the collimator-leaves 61 shifts to the position, referring to FIG. 7B, at which the X-ray radiation field E2 on the X-ray imaging is formed. The operator D makes sure the X-ray image displayed on the display element 41 located in the operation room R1, so that the operator can realize the X-ray radiation field E2 on the X-ray imaging. Under such state, the X-ray imaging is performed if needed.

Since then, when the operator D operates the aperture change switch 47 again, referring to FIG. 7A, the control element 40 controls that the collimator-leaves 61 of the collimator 12 shifts to the position at which the X-ray radiation field E1 is formed. In addition, even when a constant time passes after the operator D operates the aperture change switch 47 again to make sure the X-ray radiation field on the X-ray imaging, the control element 40 controls that the collimator-leaves 61 of the collimator 12 shift to the position at which the X-ray radiation field E1 is formed. Accordingly, the operator can continuously perform the radiation fluoroscopy following confirmation of the radiation field of the radiation on the radiation imaging.

As set forth above, the X-ray fluoroscopy imaging apparatus, according to the aspect of the present invention, allows the operator to make sure the radiation field while performing the X-ray fluoroscopy by watching the display element 41 in the operation room R1.

It will be further understood by those of skill in the art that 'leaves' is a plural of 'leaf' in that either word represents a movable portion of a structure. For example, such as a single table 'leaf' or two or more table 'leaves' to adjust a size of a table.

REFERENCE OF SIGNS

11 X-ray tube
12 Collimator
13 Table
14 X-ray detector
40 Control element
41 Display element
42 Controller
43 Operation panel
47 Aperture change switch
50 Operation panel
61 Collimator-leaves
62 Diaphragm
66 Collimator lamp
67 Mirror
69 Collimator driving element
E1 Radiation field on an X-ray fluoroscopy
E2 Radiation field on an X-ray imaging
D Operator
M Subject
R1 Operation room
R2 Examination room The steps of a method or algorithm described in connection with the embodiments disclosed herein may be embodied directly in hardware, in a software element module or circuit executed by a processor or a plurality of so-designated processors, using cloud computing, direct access, remote access, or in any combinations combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer at all currently know or understood by those of skill in the art, including artificial intelligence related computers and computational entities, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A method, using a radiation fluoroscopic apparatus capable of performing both a radiation fluoroscopy and a radiation imaging; wherein:
   said radiation fluoroscopic apparatus, further comprises:
      a radiation irradiation element that irradiates a radiation to a subject;
      a radiation detector that detects said radiation that is irradiated from said radiation irradiation element and transmits through said subject;
      a collimator with collimator-leaves that changes an area size of said radiation that is irradiated from said radiation irradiation element to said subject;
   a memory element that stores an aperture on a radiation imaging;
      a display element that displays an image that said radiation detector acquires; and
      an aperture change switch that changes said aperture, the aperture change switch being manually actuatable during the radiation fluoroscopy, operation of the aperture change switch causing the collimator-leaves to shift to a position at which an operator confirms a radiation field of the radiation imaging;
      said radiation irradiation element, said radiation detector, and said collimator are located in an examination room;
      said display and the said aperture change switch are located in an operation room;
      a control element that controls a reposition action of said collimator-leaves from a first aperture to a second aperture following at least one of (i) a passing of a constant time and (ii) a re-operation of said aperture change switch following a time since said aperture of said collimator-leaves is changed to the first aperture configuration by an operation of said aperture change switch; and
   said method, further comprising:
      a step of performing a radiation fluoroscopy;
      a step of receiving an operation of said aperture change switch while performing a radiation fluoroscopy;
      a step of calling up of said aperture on a radiation imaging, that is stored in said memory element, in accordance with receiving said operation of said aperture change switch, while performing said radiation fluoroscopy;
      a step of changing said aperture of said collimator to said aperture called up from said memory element while performing said radiation fluoroscopy;
      a step of displaying an image obtained by said radiation fluoroscopy while said aperture of said collimator is coinciding with said aperture called up from said memory element; and
      a step of repositioning said collimator-leaves from said first aperture configuration to said second aperture configuration following at least one of (i) said passing of said constant time and (ii) said re-operation of said aperture change switch following said time since said aperture of said collimator-leaves is changed to the first aperture configuration by the operation of said aperture change switch.

2. The method of claim 1, wherein:

said fluoroscopy imaging apparatus, further comprises:

two pair of opposed shifting members between said radiation irradiation element and said subject;

each said shifting member movable along a motion axis;

each said collimator-leaves attached to a bottom of each respective said shifting member opposite a diaphragm attached at a top of each said shifting member; and whereby said aperture change switch that changes said first aperture of said collimator-leaves to said second aperture configuration by changing a position of each said collimator-leave attached at said bottom of each said shifting member additionally changes a position of each said diaphragm attached at said top of each said shifting member; and said method, further comprising:

a step of moving each said shifting member along said motion axis; and a step of changing a position of each said diaphragm attached at said top of each said shifting member using said aperture change switch.

* * * * *